United States Patent
Van Den Bossche et al.

(10) Patent No.: US 9,233,194 B2
(45) Date of Patent: Jan. 12, 2016

(54) BURSITIS TREATMENT DEVICE AND METHOD

(75) Inventors: Johan Lionel Van Den Bossche, Linden (BE); Stefaan Michiel Maria Mulier, Leuven (BE); Kristoffel Pieter Maria Mulier, Hoegaarden (BE); Michiel Willem Jozef Mulier, Boutersem (BE)

(73) Assignee: Vesalius Medical Technologies BVBA, Hoegaarden (BE)

( * ) Notice: Subject to any disclaimer, the term of this patent is extended or adjusted under 35 U.S.C. 154(b) by 0 days.

(21) Appl. No.: 13/575,028

(22) PCT Filed: Jan. 26, 2011

(86) PCT No.: PCT/EP2011/000317
§ 371 (c)(1),
(2), (4) Date: Jul. 25, 2012

(87) PCT Pub. No.: WO2011/091990
PCT Pub. Date: Aug. 4, 2011

(65) Prior Publication Data
US 2012/0310149 A1  Dec. 6, 2012

(30) Foreign Application Priority Data
Jan. 26, 2010  (EP) ..................................... 10000758

(51) Int. Cl.
*A61M 1/00* (2006.01)
*A61M 5/44* (2006.01)
*A61B 18/00* (2006.01)

(52) U.S. Cl.
CPC .... *A61M 1/0058* (2013.01); *A61B 2018/00011* (2013.01); *A61M 1/0084* (2013.01); *A61M 5/44* (2013.01)

(58) Field of Classification Search
CPC ... A61M 5/44; A61M 1/0058; A61M 1/0084; A61M 2205/36; A61B 2018/00011
USPC .............................................. 604/27, 28, 113
See application file for complete search history.

(56) References Cited

U.S. PATENT DOCUMENTS 5,312,327 A * 5/1994 Bales et al. ...................... 604/21
5,322,504 A * 6/1994 Doherty et al. ............... 606/167

(Continued)

FOREIGN PATENT DOCUMENTS

DE  19754607 A1  6/1998
DE  19652381 C1  7/1998

(Continued)

OTHER PUBLICATIONS

EPO ISR, Apr. 29, 2011.

(Continued)

*Primary Examiner* — Emily Schmidt
(74) *Attorney, Agent, or Firm* — SYMBUS LAW GROUP, LLC; Clifford D. Hyra (57) ABSTRACT

A bursitis treatment device (100; 200) for treatment of inflammation of a bursa (150; 502) in a patients joint includes:
a rinsing aid;
a reservoir (101; 201) for holding the rinsing aid in fluid, freezing fluid or gaseous state;
a supply line (103; 204, 208) for transporting the rinsing aid;
a heat exchanger (104; 203) for controlling the temperature of the rinsing aid—such that the temperature of the rinsing aid enables to destroy cells causing the inflammation;
an access device (209) for injecting the rinsing aid into the bursa (150; 205); and
a drain (105; 210) for removing the rinsing aid from the bursa (150; 205) for elimination.

23 Claims, 6 Drawing Sheets

(56) References Cited

U.S. PATENT DOCUMENTS

| | | | |
|---|---|---|---|
| 5,329,936 | A | 7/1994 | Lafferty et al. |
| 5,382,229 | A | 1/1995 | Grabenkort |
| 5,616,120 | A * | 4/1997 | Andrew et al. ............... 604/28 |
| 6,193,683 | B1 * | 2/2001 | Ludin et al. ............... 604/22 |
| 6,440,103 | B1 * | 8/2002 | Hood et al. ............... 604/113 |
| 2005/0148934 | A1 * | 7/2005 | Martens et al. ............... 604/113 |
| 2005/0261626 | A1 | 11/2005 | Arai et al. |
| 2007/0179455 | A1 * | 8/2007 | Geliebter et al. ............ 604/272 |
| 2009/0124960 | A1 * | 5/2009 | Mackool ............... 604/22 |
| 2009/0163863 | A1 * | 6/2009 | Lutwyche ............... 604/119 |

FOREIGN PATENT DOCUMENTS

| | | |
|---|---|---|
| WO | 02/065930 A1 | 8/2002 |
| WO | 2009/149321 A1 | 12/2009 |

OTHER PUBLICATIONS

EPO IPRP, Apr. 23, 2012.

* cited by examiner

BURSITIS TREATMENT DEVICE AND METHOD

This application claims the benefit of European patent application No. 10000758.2, filed Jan. 26, 2010, which is hereby incorporated by reference in its entirety.

FIELD OF THE INVENTION

The present invention generally relates to the treatment of bursitis, i.e. a painful inflammation of a bursa which is a soft, fluid-filled sac that covers and cushions the relative movement between bones, tendons and muscles near the patient's joints. The invention in particular concerns a device and method for treatment of bursitis in the human or animal body on permanent basis, i.e. a device and technique that destroys all bursa membrane cells that cause the inflammation.

BACKGROUND OF THE INVENTION

Bursitis is an unsolved medical problem. Bursitis is an inflammation of a bursa or protecting sac that is located in or near the patients joints. Bursitis can be acute resulting in a sudden, sharp pain following an injury, or it can be chronic as a result of a recurrent inflammation in the same area. Most commonly, bursitis is caused by trauma, infection and crystal deposits. Bursitis typically results from overuse or injury of a joint as a consequence of intensive working or playing, poor conditioning before exercising or sporting, systematic incorrect posture at work or rest, or an abnormal positioned joint as a result of for instance arthritis or bone length differences that stress soft tissue structures in the human or animal body. Bursitis exceptionally however may also appear in association with other diseases like rheumatoid arthritis, tuberculosis, psoriatic arthritis, gout, a bacterial infection, etc.

When the joint is overused or when it stays under pressure or tension for extended periods of time, a nearby bursa or sac can become inflamed. The bursa then fills with excess fluid causing additional pressure on surrounding tissue resulting in bursitis. Bursitis usually occurs under shoulder muscles, at elbows (called epitrochlear bursitis), near the thigh or hip (called trochanteric bursitis), at heel bones (called retrocalcaneal bursitis) or kneecaps (called infrapatellar bursitis). It can also occur in the buttocks (called ischiogluteal bursitis).

Existing methods for treatment of bursitis include rest, physical therapy, protecting the inflamed area, use of anti-inflammatory drugs, surgical drainage, injection of corticosteroids and surgical removal of the bursa. An overview of state of the art treatment methods for bursitis is given in the article "*Greater Trochanteric Pain Syndrome: A Review of Anatomy, Diagnosis and Treatment*" from the authors Bryan S. Williams and Steven P. Cohen, published in "*Anesthesia & Analgesia*", Vol. 108, No. 5, May 2009, pages 1662-1670. The known bursitis treatment methods however all remove or suppress the inflammation only temporarily. Typically, the bursa grows back and the inflammation of the bursa re-appears after a few months.

Resting, physical therapy and/or treating a bursa close to the skin with padding can relieve the patients discomfort and inflammation resulting from bursitis in seven to fourteen days. Preventive measures such as the use of cushioned chairs or protective gear near joints, warm-up and cool-down exercises, avoiding overuse of joints through sports or labour, and strengthening the muscles may further help the patient in avoiding or delaying re-appearance of the bursa inflammation.

Anti-inflammatory medication used in the treatment of bursitis includes aspirin or non-steroidal drugs such as ibuprofen, naproxen or indomethacin. In case bursitis is the result of a bacterial infection, antibiotics can be used as well.

An alternative treatment consists in aspiration or surgical drainage of fluid from the bursa, and the injection of corticosteroids in the bursa. The treatment with corticosteroids however must be dosed carefully because of the long list of potential side-effects of corticosteroids.

In case of chronic bursitis that cannot be treated in the conservative way, invasive surgical removal of the bursa will be considered.

It is an objective of the present invention to disclose a device and method for the treatment of bursitis that overcomes the drawbacks and shortcomings mentioned here above in relation to the existing bursitis treatment methods. In particular, it is an objective of the present invention to disclose a device and method that enable to treat bursitis permanently, thereby avoiding recurrent appearance of the bursa inflammation.

SUMMARY OF THE INVENTION

The above defined objective is realized and the prior art shortcomings are overcome by a bursitis treatment device including:
  a rinsing aid;
  a reservoir for holding the rinsing aid in fluid, freezing fluid or gaseous state;
  a heat exchanger for controlling the temperature of the rinsing aid such that said temperature of said rinsing aid enables to destroy cells causing said inflammation;
  a supply line, coupled to the reservoir, for transporting the rinsing aid from the reservoir to the bursa;
  an access device, coupled to the supply line, for injecting the rinsing aid into the bursa; and
  a drain for removing the rinsing aid from the bursa for elimination.

Thus, the device according to the present invention enables to rinse or flush the bursa with a temperature controlled therapeutic rinsing fluid or gas, e.g. physiological water at 50° C. or hot air, thereby destroying all bursa membrane cells causing the inflammation and removing the risk for recurrent or even chronic occurrence of the inflammation. The temperature controlled therapeutic rinsing agent with caustic effect may stay a few minutes, e.g. 3 minutes, in the bursa during the so called "treatment phase". The optimal rinsing duration for bursitis treatment using the device according to the present invention depends on the therapeutic fluid or gas used, the temperature thereof, the nature and degree of inflammation, and consequently has to be determined experimentally. Thereafter, the rinsing agent is removed via the drain tube during the so called "aspiration phase".

It is noticed that the supply line and drain tube for the rinsing aid may be integrated such that a single access device, e.g. a single needle or catheter can be used for the rinsing phase and aspiration phase. Alternatively, separate pipes and needles or catheters may be foreseen. It is further noticed that the supply line may be isolated.

The reservoir may be a sac, a tank, a sterile fluid bag, etc. The use of a sterile fluid bag is preferred because the therapeutic rinsing aid can be kept sterile therein.

The heat exchanger may be located in or around the reservoir, or may be positioned in or along the supply line. The temperature must be controlled such that the temperature of the therapeutic fluid or gas in the bursa enables to destroy the bursa membrane cells causing the inflammation within an acceptable time interval of a few minutes. The logarithmic time-temperature curve at which irreversible cell necrosis occurs has been studied and published for skin treatment and may be used to select the temperature and time interval of bursitis treatment according to the present invention.

The drain may consist of a redon or a drain tube and a receptacle such as a redon bottle that is carried a period of time by the patient. Thus, after having treated the bursa with the temperature controlled therapeutic rinsing aid, the remaining rinsing fluid is eliminated from the bursa via a drain, for instance a redon or a catheter with a plurality of holes to extract the remaining fluid under vacuum, partial vacuum or sub-pressure generated via a pump. Eventually, dry gas may be flushed through the bursa as part of this drying phase in order to remove the last droplets or vapour of the rinsing aid from the bursa. The drying phase will enhance the adhesion of top and bottom layer of the bursa.

Optionally, the access device in the bursitis treatment device may include one or more of the following, perforated or not:
 a needle;
 a trocar;
 a Veress needle;
 a catheter;
 a spray; and
 a nozzle.

The above listed access devices can be separate or combined, adjacent or concentric. The catheters can be straight, bent or curled. The end of the curl can be attached to the needle or trocar by means of a wire. The catheters can be coated by an agent that improves sliding, such as Teflon. A radio-opaque wire can be incorporated in the catheter. Insertion of the access device preferably takes place under radiological control and/or ultrasound control.

Depending on the state of the rinsing aid—fluid or gas—and its temperature, it may be advantageous to use an injection needle, a Veress needle, a catheter perforated with holes, or even a spray with nozzle. Any of these implementations will have to be cusped for intrusion in the human or animal body and for puncturing the bursa wall. A Veress needle may be preferred because it is designed to avoid double perforation of the bursa. The spring and pestle which inherently form part of such a Veress needle will prevent a second perforation of the bursa wall once the tip of the Veress needle has entered the bursa. Plural needles or catheters may be foreseen depending on the attainable pressure and flow rate.

In general, tests have demonstrated that for the application of bursitis treatment according to the current invention, a perforated catheter surrounding an injection needle is preferred as access device. Whereas the needle enables to inject the rinsing aid in the bursa, the perforated catheter ensures complete removal of the rinsing aid after the treatment. Plural perforations in the catheter avoid blockage of the drain, even if one or a few perforations would become blocked as a result of tissue aggregation. The perforated catheter may be made of plastic or thermoplastic material or other material that can be sterilized for insertion in the body.

Advantageously, the access device is supplemented with a device or piece that aspires moisture. This piece may also be useful when manually irrigating the bursa and verifying drainage.

Optionally, the access device in the bursitis treatment device may include a guide.

Such guide may assist in bringing the needle or catheter in the bursa.

Further optionally, the access device in the bursitis treatment device may comprise one or more of the following:
 a temperature sensor;
 a pressure sensor; and
 a flow sensor.

The optional temperature sensor, pressure sensor, flow sensor or a combination of sensors may be integrated in the needle or catheter that intrudes the bursa during the treatment. An advantage thereof is that the temperature in the bursa, pressure in the bursa, flow rate, or a combination thereof can be measured very accurately and can serve as input for controlling the reservoir temperature, the supply line temperature, the container pressure and/or the flow rate. A controller of these parameters that will be described further in this patent application may operate in an automated fashion on the basis of sensory input.

According to another optional aspect, the bursitis treatment device further includes:
 a camera mounted on the syringe.

Thus, the bursitis treatment method according to the invention may be complemented with arthroscopic treatment using an inspection camera. Such inspection camera enables to visibly inspect the inside of the bursa which enables the physician or operator of the bursitis treatment device to inspect the correct location of the insertion device with respect to the bursa, to determine the size and extension of the bursa, to exclude extravasation and/or pre-existing connections to the joint space. After the treatment, the camera also enables to draw conclusions with respect to effectiveness of the treatment and eventual duration or repetition of the treatment process. In order to better visualize eventual fistula, a contrasting fluid may be used.

The supply line and drain for injecting and removing a fluid into and from the bursa in the bursitis treatment device may be thermally isolated. The needle(s) or catheter(s) for injecting or removing the fluid may be isolated by for instance ceramic coating, plastic coating, or another isolation technique. Alternatively, a double-walled needle or access device with vacuum space between the two walls could be used. The objective thereof is to reduce the outside temperature, for instance by 5° C., such that no damage is caused to the surrounding cells in the treatment period that may for instance last for 200 seconds. To avoid burning the patient's skin, the needle or access device may further be supplemented with an isolating, preferably cone-shaped element that isolates the skin and eventually also tissue between the skin and bursa from direct contact with the access device that transports the heated rinsing aid. A cone shaped element is preferred to ease insertion, but alternate shapes may be considered as well for the isolating element. Preferably, such isolating element is slidably mounted on the access device such that the injection depth of the access device remains controllable. The sliding isolating element may for instance be made out of rubber.

Advantageously, the access device and drain in the bursitis treatment device are integrated into an insertion device comprising at least a first lumen for injection of the rinsing aid in the bursa and a second lumen for drainage of the rinsing aid, the second lumen being equipped with multiple drainage holes.

Indeed, injection and drainage of the rinsing aid may be combined in a single device. The plural holes guarantee continued drainage even when one or a few holes become obstructed through vessels or constituents in the drained fluid. Additional lumen may be integrated, e.g. to enable injection of additives. The plural lumen may be realized concentrically (e.g. a double wall or triple wall lumen), or may be realized side-by-side. Side-by-side lumen may be wrenched over the entire length or a tip portion, or may be spring-rotated in order to control the distance between successive drainage holes.

Still optionally, the bursitis treatment device may comprise:
  a spectrometer for measuring colour fading of the wall of the bursa.

Through a colorimeter or spectrometer that for instance projects light in the bursa via the needle or catheter, and that guides the reflected light via the same needle or catheter onto a sensor, the bursitis treatment device may be enabled to sense and analyse the colour spectrum and to measure as a result thereof the degree of non-viability of the bursa membrane cells inside the bursa. Again, this is useful information for controlling the duration of the treatment.

Optionally, the bursitis treatment device according to the invention may comprise:
  a heat sensitive camera.

Such heat sensitive camera may be used to control the distribution of the rinsing aid and the coldest spot in the bursa such that non-viability of all bursa membrane cells that cause the inflammation is guaranteed.

The rinsing aid may consist of:
  a hypertonic saline;
  an alcohol;
  acetic acid;
  steam;
  demineralised water; or
  another caustic agent.

Obviously, alternative products or solutions may be excellent rinsing aids with caustic effect for use in the bursitis treatment device according to the invention. The skilled person will appreciate that the inventive nature of the device does not lie in the use of a particular rinsing aid and it is consequently not the intention to restrict applicability of the invention to any particular choice of rinsing aid.

Further optionally, the bursitis treatment device may comprise:
  a second reservoir for holding a second rinsing aid in fluid, freezing fluid or gaseous state for pre-treatment of the bursa; and/or
  a third reservoir for holding a third rinsing aid in fluid, freezing fluid or gaseous state for post-treatment of the bursa.

Thus, in an optional pre-treatment phase, the bursa can be rinsed with physiological water or gas or another neutral rinsing aid (e.g. salina) at a temperature between 0° C. and 150° C. As a result of the pre-treatment phase, the in- and outflow, working pressures and flow are optimised.

In an optional post-treatment phase, the bursa is rinsed with for instance a pharmacologic active constituent in order to remove all caustic agents. Thereafter, a suction technique is applied in the so called "aspiration phase" to empty the bursa under vacuum, partial vacuum or sub-pressure.

Optionally, the bursitis treatment device further comprises means for controlling one or more of the following parameters:
  temperature in the supply line;
  temperature in the reservoir;
  temperature in the bursa;
  temperature in the outflow line;
  pressure in the reservoir;
  pressure in the supply line;
  pressure in the bursa;
  pressure in the outflow line;
  flow rate of the rinsing aid; and
  time interval for injecting the rinsing aid.

In other words, the bursitis treatment device according to the invention may be fully programmable with respect to temperature, pressure, flow rate and run time. The control of temperature and pressure may be assisted by temperature sensors and pressure sensors as indicated here above. Thanks to the controlled temperature, and the eventual killing nature of the rinsing aid, membrane cells on the inside of the bursa will be destroyed. In case of pre-treatment and/or post-treatment phase, the temperature, pressure, flow rate and time interval parameters for these phases of the treatment method may be controllable as well. The parameters may be adjustable through buttons, knobs, touch screens, etc. and hardware such as a heating element, a pump, a clock or timer integrated in the treatment device. Alternatively, the parameters may be controlled from a PC, terminal, remote control, etc. connected directly or via a network to a control interface of the bursitis treatment device.

In order to control the temperature of the rinsing aid such that the temperature of the fluid injected in the bursa changes to the desired heating temperature abruptly, the needle or access device may be equipped with a valve, e.g. a thermostatic valve, and an electronic temperature sensor. The valve will remain closed as long as the temperature of the rinsing aid in the supply line stays below a desired, predefined temperature, and the rinsing aid shall be removed, e.g. towards a waste container for elimination. The valve will open as soon as the desired, set-point temperature of e.g. 60° C. is reached. This way, the temperature where the bursa is exposed to shall describe a step function, which increases the effectiveness of the treatment. As long as the temperature of the rinsing aid is below the desired temperature, the fluid shall be prevented from entering the bursa and shall be guided towards a waste container for elimination. This enables for instance to deal with slow, gradual increase of the temperature due to lengthy supply lines, e.g. bridging several meters of distance between the reservoir and the access device Another option of the bursitis treatment device, consists in a memory for storing one or more of the following:
  preset and/or measured temperature values;
  preset and/or measured pressure values;
  preset and/or measured flow rate values; and
  preset and/or measured time interval values.

Thus, the measured parameter values such as reservoir, supply line or bursa temperature, reservoir or bursa pressure, flow rate, and duration of the different phases may be logged and stored in a data file. Also the preset target temperatures, pressures, flow rates and time intervals may be stored in such memory.

Optionally, the drain in the bursitis treatment device includes one or more of the following:
  a cell counter; and
  a chemical sensor for detection of cell constituents.

This way, it becomes possible to detect when the number or density of cell constituents has dropped below a certain threshold, and this information may serve as input to control the duration of the treatment.

Also optionally, the bursitis treatment device may include:
  a leakage detector.

The leakage detector serves as an instrument for quality control of the bursitis treatment device. If total inflow and total outflow are not equal, there might be a leakage with danger for the patient. In this case, the pump may be de-activated or the entire device may be de-activated automatically.

The bursitis treatment device further optionally includes:
  a data interface.

Hence, the above mentioned data file may be ported to another device, e.g. a PC or network, via a wired or wireless data interface such as a Universal Serial Bus (USB), a Bluetooth interface, a WiFi interface, an Ethernet connection, etc.

A corresponding bursitis treatment method includes the steps of:
- insertion of an access device in the bursa;
- injecting via a supply line, coupled between a reservoir and the access device, a temperature controlled rinsing aid into the bursa;
- controlling the temperature of the rinsing aid such that the temperature of the rinsing aid enables to destroy cells causing the inflammation; and
- removing via a drain the rinsing aid from the bursa for elimination.

Optionally, the bursitis treatment method may include one or several of the following steps:
- insufflating the bursa thereby breaching inner adhesions;
- imaging of the bursa with radio-opaque contrast medium;
- pre-treatment of the bursa by injecting a second rinsing aid before injection of the rinsing aid; and/or
- post-treatment of the bursa by injecting a third rinsing.

Whereas insufflating enables to breach pre-existing inner adhesions, pre-treatment with a contrast agent enables to verify and inspect the correct location of the insertion device with respect to the bursa, determine the size and extension of the bursa, and exclude extravasation and/or pre-existing connections to the joint space. The pre-treatment rinsing phase enables to optimise the in- and outflow, working pressures and flow. The post-treatment rinsing phase removes all caustic agents.

Optionally, the bursitis treatment method may include the step of:
- electrically charging the bursa.

Electrically charging the bursa, enables to deposit certain active constituents on the wall of the bursa during the treatment.

Further optionally, the bursitis treatment method may include the additional step of:
- gluing membrane surfaces of the bursa using a biocompatible glue.

In the optional gluing phase, the membrane walls of the bursa are stuck together.

A corresponding cyst treatment device for treatment of a cyst in a patient includes:
- a rinsing aid;
- a reservoir for holding the rinsing aid in fluid, freezing fluid or gaseous state;
- a heat exchanger for controlling the temperature of the rinsing aid such that the temperature of the rinsing aid enables to destroy cells of interlining of the cyst;
- a supply line, coupled to the reservoir, for transporting the rinsing aid from the reservoir to said cyst;
- an access device, coupled to the supply line, for injecting the rinsing aid into said cyst; and
- a drain for removing the rinsing aid from the cyst for elimination.

Indeed, a cyst is a closed sac consisting of a membrane filled with gaseous, fluids or semi-solid material. Such cyst can be treated by necrosis of cells of the interlining through the device according to the present invention.

Furthermore, a bursitis treatment device for treatment of inflammation of a bursa in a patient includes:
- means for inserting a balloon or sac in the bursa;
- a rinsing aid;
- a reservoir for holding the rinsing aid in fluid, freezing fluid or gaseous state;
- a supply line, coupled to the reservoir, for transporting the rinsing aid from the reservoir to the balloon or sac;
- an access device, coupled to the supply line, for injecting the rinsing aid into the balloon or sac;
- a heat exchanger for controlling the temperature of the rinsing aid such that a temperature of a wall of the balloon or sac enables to destroy cells causing the inflammation; and
- a drain for removing the rinsing aid from the balloon or sac for elimination.

Indeed, the rinsing aid need not be directly in contact with the cells to be destroyed but may be injected in a balloon or sac that is first inserted in the patient's body to represents an artificial cyst therein. The temperature of the rinsing aid then is controlled in such a way that the temperature of the wall of the balloon or sac enables to destroy cells during the temperature treatment.

The heat exchanger may be heating or cooling the rinsing aid, or may be able to perform both. Cooling may for instance be realized through use of liquid nitrogen, or through injection of chlorofluorocarbons (CFCs) that cool the wall of the balloon or sac through evaporation.

It is further noticed that the balloon or sac may for instance be provided around the catheter or access device for insertion in the patient's body.

DETAILED DESCRIPTION OF EMBODIMENT(S)

Figure 1:
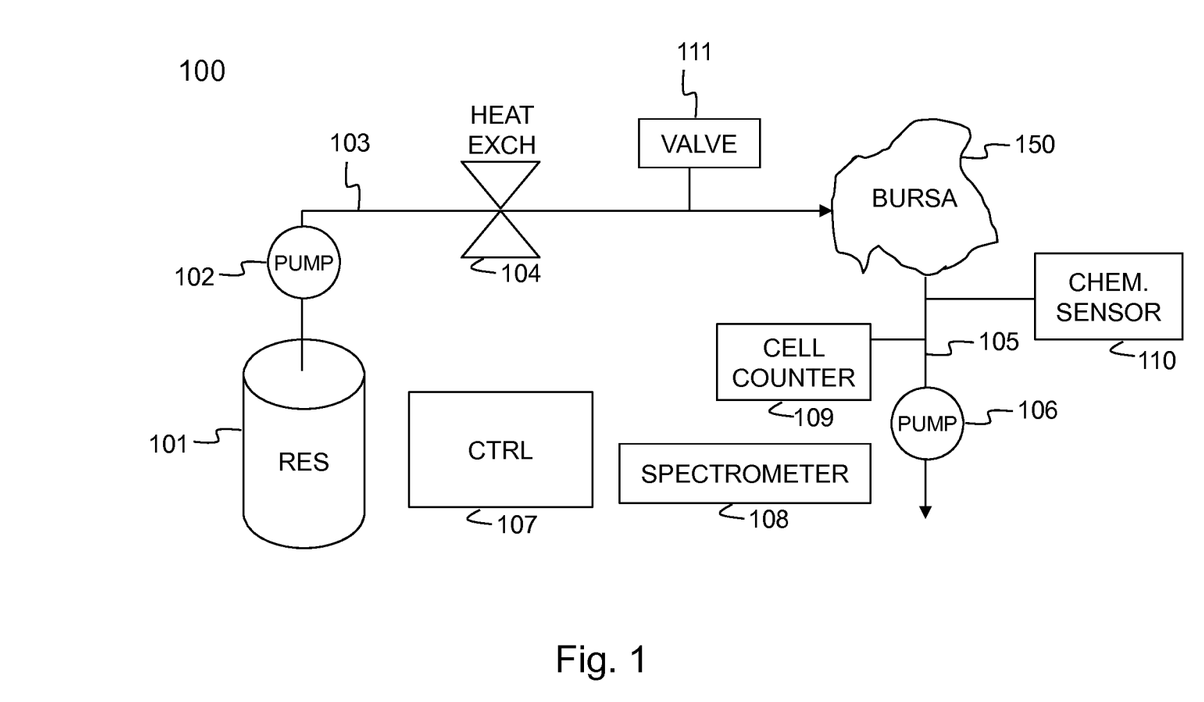
FIG. 1 illustrates a first embodiment of the bursitis treatment device according to the present invention.

The bursitis treatment device 100 illustrated by FIG. 1 has one reservoir for a therapeutic fluid, 101 or RES, and a supply line 103 from the reservoir 101 to an access or insertion device in the bursa 150. The bursitis treatment device 100 contains a pump 102 and a heat exchanger, 104 or HEAT EXCH, along the supply line 103. A drain tube 105 with pump 106 extends from the bursa 150. The supply line 103 and the drain tube 105 are supposed to be inserted in the bursa 150 through two separate access devices, i.e. two needles that are not shown in detail in FIG. 1. FIG. 1 further shows a controller 107, spectrometer 108, cell counter 109, chemical sensor 110 and valve 111 that may form part of the bursitis treatment device 100.

The reservoir 101 holds rinsing aid at ambient temperature. The reservoir 101 may be open but preferably is closed for reasons of sterility. In the insertion phase, the access devices are inserted in the bursa under radiological and/or ultrasound control. Thereafter, inner adhesions pre-existing in the bursa are breached in the insufflation phase during which the bursa is filled and expanded using carbondioxide or an alternate gas. In the verification phase, a contrast agent is injected in the bursa to inspect the correct location of the insertion device with respect to the bursa, to determine the size and extension of the bursa, and to exclude extravasation and or pre-existing connections to the joint space. The in- and outflow, as well as the working pressures are optimised in a pre-treatment phase where the bursa is rinsed with neutral rinsing aid. In the treatment phase, the pump 102 transfers an active temperature controlled rinsing agent with caustic effect from the reservoir 101 to the bursa 150 in order to fill the bursa 150 with the therapeutic fluid. Along the supply line 103, the rinsing agent is temperature controlled by the heat exchanger 104, e.g. up to the desired temperature of 50° C., such that temperature controlled rinsing agent is pumped into the bursa 150. The bursa is rinsed with the temperature controlled rinsing aid for a desired time interval of about 3 minutes in order to hold the bursa for about 3 minutes at the desired temperature of 50° C. thereby destroying the bursa membrane cells that cause the inflammation. Outflow is performed with the second pump 106. Thereafter, in the so-called post-treatment phase, the caustic agent is removed by rinsing the bursa with neutral rinsing aid. Thereafter, in the so-called aspiration phase, the first pump 102 is inactivated and only the second pump 106 remains activated to remove the remaining rinsing aid from the bursa 150 via drain 105. Eventually, biocompatible glue may be used to stick together the bursa membrane walls.

The controller 107 controls the hardware in the bursitis treatment device 100: it activates/de-activates the pumps 102 and 106, it controls the flow rate in the supply line 103, and it controls the heat exchanger 104 in order to obtain the desired temperature of 50° C. The controller 107 may receive feedback from a temperature sensor in the supply line 103 or in the bursa 150, and use the reported temperatures to control the heat exchanger 104. The controller may also receive feedback from a pressure sensor in the bursa, from a flow sensor, or from a thermal camera to obtain more precise information on the temperature distribution in the bursa and more particularly along the membrane surface of the bursa. This information will enable the controller to more adequately control the flow rate and temperature of the rinsing aid, and to control the time interval for the different phases of the treatment. A sensor for cell particles in the drain tube 105 may provide input to the controller 107 enabling the controller 107 to stop the therapeutic treatment only when the fraction of cell particles has dropped below a certain threshold. Alternatively, an inspection camera may be provided for combined arthroscopy. The inspection camera may be integrated with the supply line 103, may be integrated with the drain 105, may be integrated with the access or insertion device, or may be brought into the bursa independently from the supply and drain. The feedback from such camera may also be used by the controller 107 to control the duration of the different phases. Further a leakage detector may provide information to the controller 107 enabling the latter to switch off the entire device 100.

Whereas the pump 12 is drawn in the supply line 103, a variant embodiment of the pump may consist of a cover holding a bag of physiologic water that is held under pressure via a hand-operated pressure bulb. In this embodiment of the pump, the pressure may be indicated by a pressure indicator on the cover.

Figure 2:
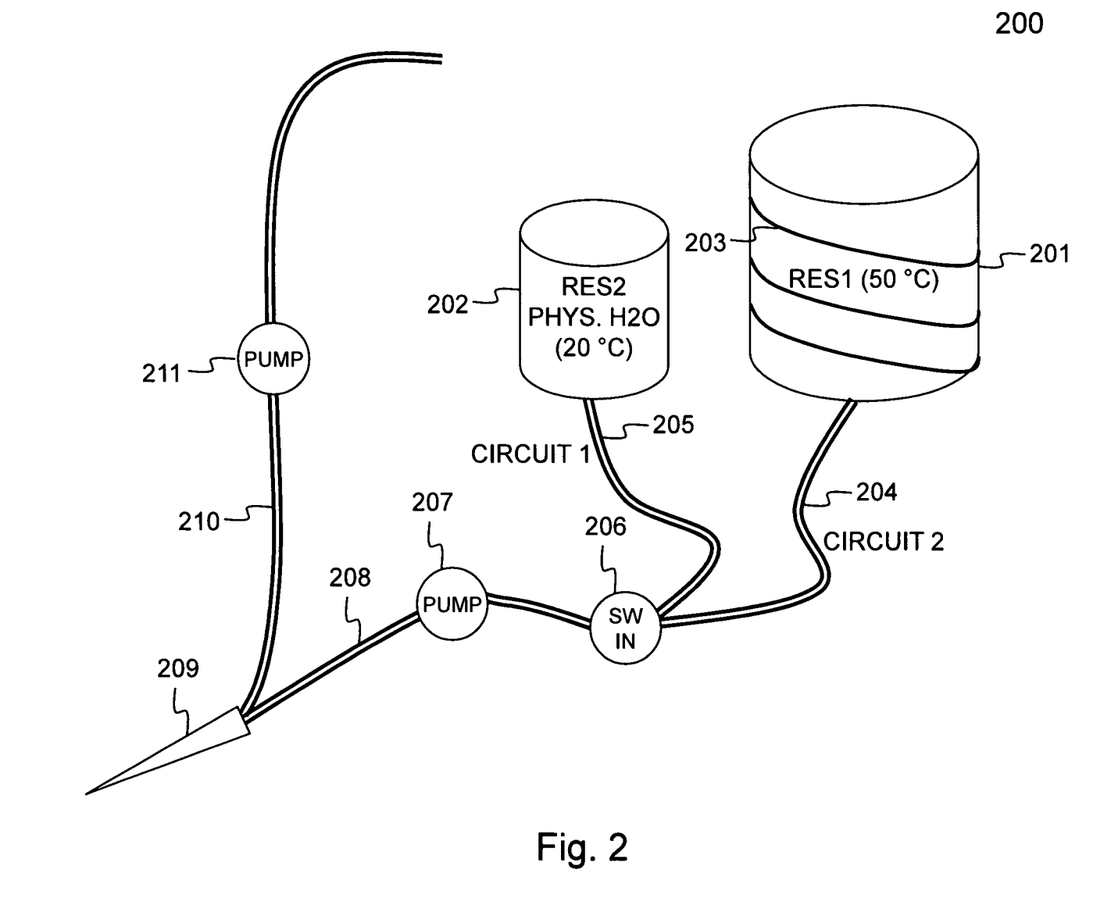
FIG. 2 illustrates a second embodiment of the bursitis treatment device according to the present invention.

FIG. 2 shows a variant embodiment 200 having two reservoirs, a first reservoir, 201 or RES1, with a heat exchanger 203, and a second reservoir, 202 or RES2. A first supply line 204 couples the first reservoir 201 to a first intake of a switch, 206 or SWITCH IN. Similarly, a second supply line 205 couples the second reservoir 202 to a second intake of the switch 206. A third supply line 208 extends from the switch 206 to access device 209. Along this third supply line 208, the burst treatment device 200 contains a first pump 207. A drain 210 with second pump 211 extends from the access device 209 to a receptacle not shown in FIG. 2.

Thanks to the second reservoir 202 and the manual or automatic switch 206, the bursa can be filled and expanded in a pre-treatment phase with physiological water, PHYS. H2O, kept at 20° C. in the second reservoir 202, without having to remove or replace reservoirs. Alternatively, a gas like carbondioxide or CO2 may be used in the pre-treatment phase. Such gas can be drained faster and enables to breach inner adhesions and completely open the bursa through inflation thereby preparing the bursa optimally for the therapeutic phase. After a few minutes, the pre-treatment phase is stopped and the switch 206 is changed such that demineralised water kept at 50° C. in the first reservoir 201 is now pumped into the bursa. In this therapeutic treatment phase, the temperature controlled demineralised water will have a lethal effect on cells at the bursa surface that have caused the inflammation. Just like the rinsing fluid or CO2 gas, the therapeutic temperature controlled demineralised water is injected in the bursa via access device 209. Outflow is performed with the second pump 211. Here below, the access device 209 will be described in more detail with reference to FIG. 3 and FIG. 4. It serves as single insertion device during the different phases whereto both the inlet or supply line 208 and the outlet or drain tube 210 are coupled. After the therapeutic phase, the caustic agent is removed by rinsing the bursa with neutral rinsing aid. Thereafter, pump 207 becomes de-activated whereas pump 211 remains activated to start the aspiration phase. The fluid in the bursa is now drained via drain tube 210. As a result, the bursa deflates and the bursa membrane claps together. Regeneration of the cells causing inflammation of the bursa is avoided which definitively resolves the bursitis.

In an optional additional phase, the bursa may be flushed with fluid at 37° C. to avoid spreading of the water in the patient's body. In other words, in the post-treatment phase the bursa is rinsed out to remove all caustic agents.

A further optional step consists in the application of Tissuecol or another fibrin glue on the bursa surface. For an average size bursa, the application of for instance 0.5 ml biocompatible glue will suffice. The aim of the biocompatible glue is to stick together the membrane surfaces after the therapeutic treatment.

It is noticed that the pre-treatment phase wherein the bursa is flushed with water or CO2 to breach pre-existing inner adhesions may be executed in a pulsated way: alternately the fluid or gas will be injected in the bursa via the needle and sucked away from the bursa via the needle. The pulsating pre-treatment has as advantage that obstruction of the needle as a result of fibrin or clotting of loose tissue in the bursa is avoided.

Figure 3:
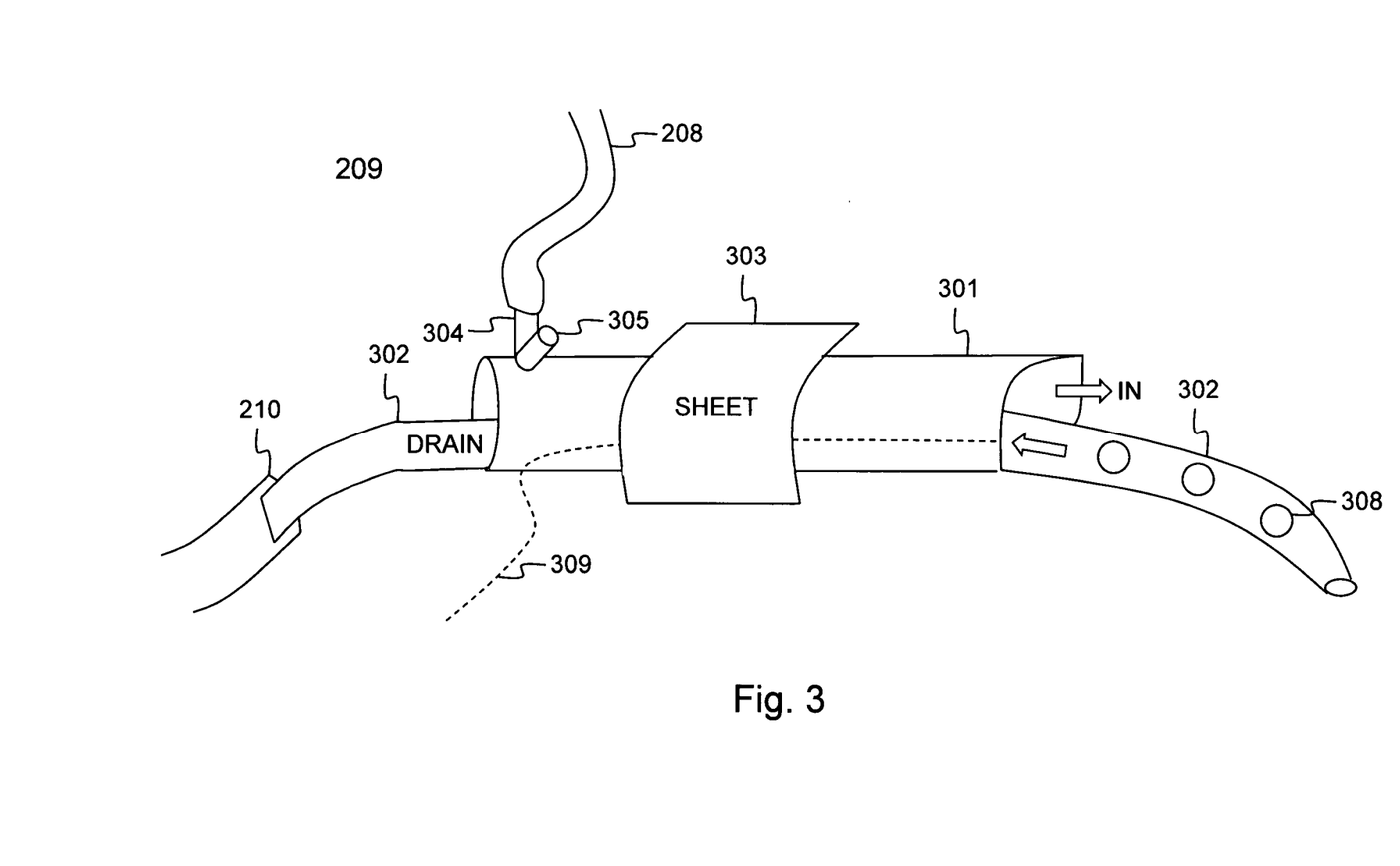
FIG. 3 illustrates the access device of an embodiment of the bursitis treatment device according to the present invention.
Figure 4:
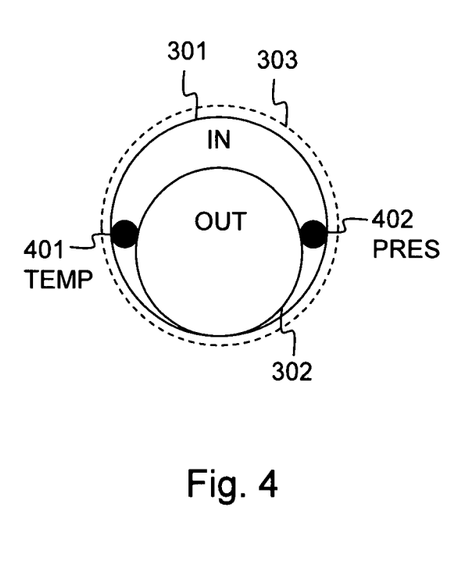
FIG. 4 is a detailed cross-section of the access device shown in FIG. 3.

FIG. 3 and FIG. 4 illustrate the access or insertion device 209 of FIG. 2 in more detail. The access device 209 has a needle 503 that is covered with a sheet 303. Within the needle 301, the access device 209 has a redon 502 or catheter with plural perforations 508 through which the fluids or gasses are sucked away from the bursa. FIG. 3 and FIG. 4 also show the presence of a temperature sensor, 403 or TEMP, and a pressure sensor, 404 or PRES, that feed back the temperature and pressure measured in the bursa via wiring 309. The supply line 208 is connected to a first inlet 304 of the needle 301. An additional inlet 305 is foreseen for injecting for instance fluids in the bursa via the same access device 209. To the outlet of the redon 302, the drain tube 210 is connected.

Figure 5:
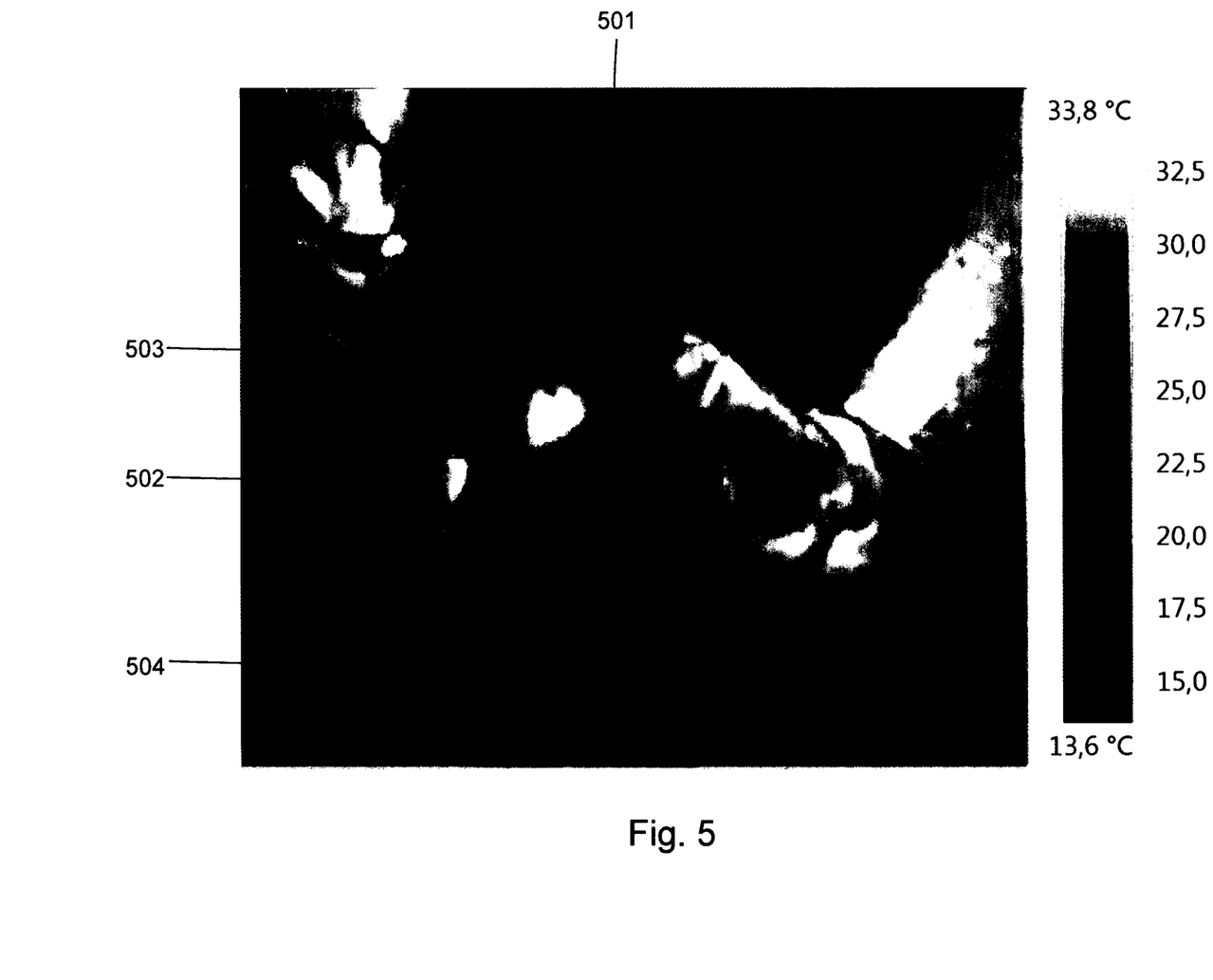
FIG. 5 is an IR image of a bursa that is therapeutically treated according to the method of the invention.

FIG. 5 at last shows an IR image of a bursa 502 near a bone 501 that is therapeutically treated with temperature controlled demineralised water injected via a first access device 503 and drained via a second access device 504. When interpreted together with the temperature scale on the rightmost side of the figure, FIG. 5 illustrates very well the temperature distribution in the bursa. In order to destroy all cells causing inflammation of the bursa and avoid regeneration of the bursitis, it is important that the entire bursa surface is temperature controlled evenly. FIG. 5 illustrates that this is the case using the invented method.

Figure 6:
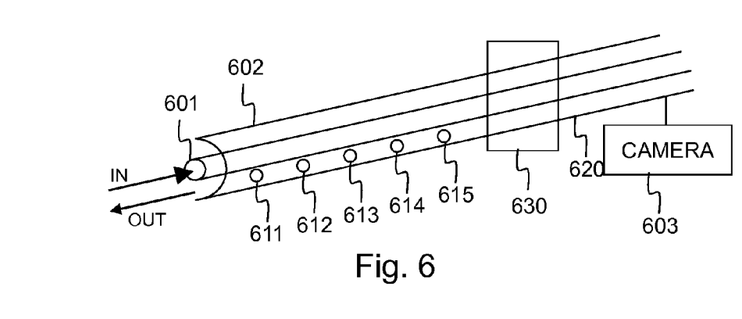
FIG. 6 illustrates a preferred device for access/drainage.
Figure 7:
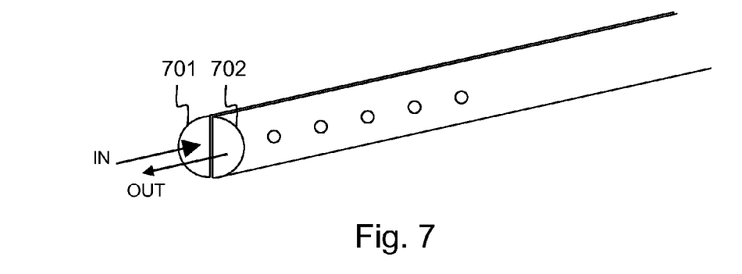
FIG. 7 illustrates a variant embodiment of the preferred device for access/drainage.

FIG. 6 and FIG. 7 show insertion devices that contain a first lumen, 601 or 701, for injection of fluids and a second lumen, 602 or 702, for drainage of fluids. Additional lumen may be included, e.g. to enable injection of additives. The lumen used for drainage, 602 or 702, is equipped with multiple drainage holes, 611, 612, 613, 614 and 615 in FIG. 6. The plural holes guarantee continued drainage even when one or a few holes become obstructed through vessels or constituents in the drained fluid. Lumen 602 may have a double wall 620 with vacuum space in between, a sliding, isolating element 630 and a camera 603.

Figure 8:
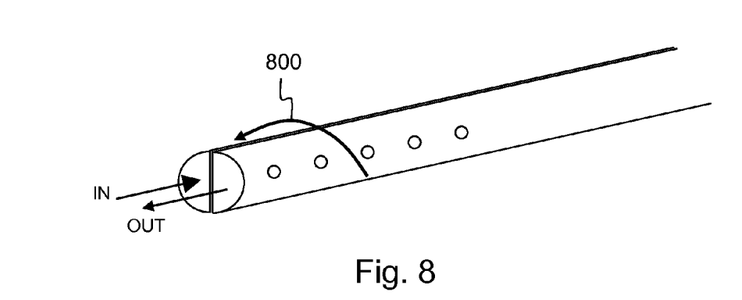
FIG. 8 illustrates another variant embodiment of the preferred device for access/drainage.

The plural lumen may be realized concentrically as illustrated by FIG. 6 (e.g. a double wall or triple wall lumen), or may be realized side-by-side as illustrated by FIG. 7. Side-by-side lumen may be wrenched over the entire length or a tip portion, as indicated by arrow 800 in FIG. 8, or may be spring-rotated in order to control the distance between successive drainage holes.

Although the present invention has been illustrated by reference to specific embodiments, it will be apparent to those skilled in the art that the invention is not limited to the details of the foregoing illustrative embodiments, and that the present invention may be embodied with various changes and modifications without departing from the scope thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. In other words, it is contemplated to cover any and all modifications, variations or equivalents that fall within the scope of the basic underlying principles and whose essential attributes are claimed in this patent application. It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", "third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above.

The invention claimed is:

1. A bursitis treatment device for treatment of inflammation of a bursa in a patient, said bursitis treatment device comprising:
    a rinsing aid;
    a reservoir for holding said rinsing aid in fluid, freezing fluid or gaseous state;
    a heat exchanger for controlling the temperature of said rinsing aid such that said temperature of said rinsing aid destroys the bursa cells causing the inflammation within a few minutes;
    a supply line, coupled to said reservoir, for transporting said rinsing aid from said reservoir to the bursa;
    an access device, coupled to said supply line, for injecting said rinsing aid into the bursa, said access device being shaped and sharpened for penetration of the patient's skin, underlying tissue, and a bursa wall of the bursa; and
    a drain for removing said rinsing aid from the bursa for elimination;
    wherein the bursa resides under the patient's shoulder muscles, at the patient's elbow, causing epitrochlear bursitis, near the patient's thigh or hip, causing tronchanteric bursitis, at the patient's heel bones, causing retrocalcaneal bursitis, at the patient's kneecaps, causing infrapatellar bursitis, or in the patient's buttocks, causing ischiogluteal bursitis.

2. A bursitis treatment device according to claim 1, wherein said access device comprises one or more of the following, perforated or not:
    a needle;
    a trocar;
    a Veress needle;
    a catheter; and
    a nozzle.

3. A bursitis treatment device according to claim 1, wherein said access device further comprises a guide.

4. A bursitis treatment device s according to claim 1, wherein said access device further comprises one or more of the following:
    a temperature sensor;
    a pressure sensor; and
    a flow sensor.

5. A bursitis treatment device according to claim 1, further comprising:
    a camera mounted on said access device.

6. A bursitis treatment device according to claim 1, further comprising:
    a thermally isolated supply line, access device, and drain for injecting and removing a fluid into and from the bursa.

7. A bursitis treatment device according to claim 6, wherein said thermally isolated access device comprises a double wall with vacuum space in between.

8. A bursitis treatment device according to claim 6, further comprising:
    a sliding, isolating element around said access device for isolating skin and tissue from direct contact with said access device.

9. A bursitis device according to claim 1,
    wherein said access device and said drain are integrated into an insertion device comprising at least a first lumen for injection of said rinsing aid in the bursa and a second lumen for drainage of said rinsing aid, said second lumen being equipped with multiple drainage holes.

10. A bursitis treatment device according to claim 1, further comprising:

a spectrometer for measuring colour fading of the wall of the bursa.

11. A bursitis treatment device according to claim 1, further comprising:
a heat sensitive camera.

12. A bursitis treatment device according to claim 1, wherein said rinsing aid comprises either:
a hypertonic saline;
an alcohol;
acetic acid;
steam;
CO2;
demineralised water; or
another caustic agent.

13. A bursitis treatment device according to claim 1, further comprising:
a second reservoir for holding a second rinsing aid in fluid, freezing fluid or gaseous state for pre-treatment of the bursa; and/or
a third reservoir for holding a third rinsing aid in fluid, freezing fluid or gaseous state for post-treatment of the bursa.

14. A bursitis treatment device according to claim 1, further comprising means for controlling one or more of the following parameters:
temperature in said supply line;
temperature in said reservoir;
temperature in the bursa;
temperature in an outflow line of said drain;
pressure in said reservoir;
pressure in said supply line;
pressure in the bursa;
pressure in an outflow line of said drain;
flow rate of said rinsing aid; and
time interval for injecting said rinsing aid.

15. A bursitis treatment device according to claim 14, further comprising:
a thermally controlled valve in said supply line or said access device, said thermally controlled valve being adapted to open as soon as said rinsing aid in said supply line has reached a certain, predefined temperature.

16. A bursitis treatment device according to claim 1, further comprising a memory for storing one or more of the following:
preset and/or measured temperature values;
preset and/or measured pressure values;
preset and/or measured flow rate values; and
preset and/or measured time interval values.

17. A bursitis treatment device according to claim 1, wherein said drain comprises one or more of the following:
a cell counter; and
a chemical sensor for detection of cell constituents.

18. A bursitis treatment device-according to claim 1, further comprising:
a leakage detector.

19. A bursitis treatment device according to claim 1, further comprising:
a data interface.

20. A bursitis treatment device according to claim 1, wherein the access device is a Veress needle.

21. A bursitis treatment device according to claim 1, wherein the supply line, access device and heat exchanger are configured to fill the bursa with the rinsing aid and hold the entire bursa wall at said temperature evenly for a few minutes so that the bursa cells causing the inflammation are destroyed.

22. A bursitis treatment device according to claim 1, wherein the bursa resides in the patient's buttocks, causing ischiogluteal bursitis, and wherein the access device is at least 3 cm long.

23. A bursitis treatment method for treatment of inflammation of a bursa in a patients joint, said bursitis treatment method comprising the steps of:
insertion of an access device shaped and sharpened for penetration of the patient's skin, underlying tissue, and bursa wall in the bursa;
injecting via a supply line, coupled between a reservoir and said access device, a temperature controlled rinsing aid into the bursa;
controlling the temperature of said rinsing aid such that said temperature of said rinsing aid destroys bursa cells causing the inflammation within an acceptable time interval of a few minutes; and
removing via a drain said rinsing aid from the bursa for elimination;
wherein the bursa resides under the patient's shoulder muscles, at the patient's elbow, causing epitrochlear bursitis, near the patient's thigh or hip, causing tronchanteric bursitis, at the patient's heel bones, causing retrocalcaneal bursitis, at the patient's kneecaps, causing infrapatellar bursitis, or in the patient's buttocks, causing isichiogluteal bursitis.

* * * * *